(12) United States Patent
Mentzer

(10) Patent No.: US 9,080,984 B2
(45) Date of Patent: Jul. 14, 2015

(54) BLAST, BALLISTIC AND BLUNT TRAUMA SENSOR

(71) Applicant: U.S. Army Research Laboratory ATTN:RDRL-LOC-I, Adelph, MD (US)

(72) Inventor: Mark Andrew Mentzer, Churchville, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 13/737,985

(22) Filed: Jan. 10, 2013

(65) Prior Publication Data

US 2013/0189795 A1 Jul. 25, 2013

Related U.S. Application Data

(60) Provisional application No. 61/589,005, filed on Jan. 20, 2012.

(51) Int. Cl.
| | |
|---|---|
| *G01N 33/53* | (2006.01) |
| *G01N 21/78* | (2006.01) |
| *G01N 33/543* | (2006.01) |
| *G01N 33/58* | (2006.01) |
| *G01N 33/68* | (2006.01) |

(52) U.S. Cl.
CPC ............ *G01N 21/78* (2013.01); *G01N 33/5432* (2013.01); *G01N 33/54366* (2013.01); *G01N 33/582* (2013.01); *G01N 33/6896* (2013.01); *G01N 2500/00* (2013.01); *G01N 2800/28* (2013.01); *G01N 2800/40* (2013.01)

(58) Field of Classification Search
None
See application file for complete search history.

(56) References Cited

U.S. PATENT DOCUMENTS

| | | | | |
|---|---|---|---|---|
| 6,387,614 | B1 * | 5/2002 | Cheng et al. | ...................... 435/4 |
| 7,433,727 | B2 | 10/2008 | Ward et al. | |
| 2010/0028902 | A1 * | 2/2010 | Brown et al. | .................. 435/7.1 |
| 2010/0151553 | A1 * | 6/2010 | Bjork et al. | ................ 435/173.7 |

OTHER PUBLICATIONS

Zhang et al. (Analytical Biochem 1995 vol. 229, p. 291-298).*
Mentzer et al. (J. Biol. Chem. 2001 vol. 276, p. 15575-15580).*
Chen et al. (J. Nanoparticle Res 2006 vol. 8, p. 1033-1038).*
Sklar et al. (J. Biol. Chem. 1981 vol. 256, p. 4286-4292).*
Ladokhin et al. J. Membrane Biol. 2010 vol. 236, p. 247-253.*
Epand et al. Biopolymers 2003 vol. 71, p. 2-16.*

* cited by examiner

*Primary Examiner* — Jacob Cheu
(74) *Attorney, Agent, or Firm* — Robert Thompson

(57) ABSTRACT

A molecular biosensor is provided including a lipid vesicle and a housing wherein the vesicle is contained on or within the housing and where the housing has a portion capable of transmitting a force generated, external to the housing to the vesicle. The biosensor is used in processes of detecting the presence or absence of an event force such as a blast or blunt force sufficient to produce a medical complication such as traumatic brain injury.

6 Claims, No Drawings

BLAST, BALLISTIC AND BLUNT TRAUMA SENSOR

CROSS REFERENCE TO RELATED APPLICATIONS

This application depends from and claims priority to U.S. Provisional Application No. 61/589,005 filed Jan. 20, 2012, the entire contents of which are incorporated herein by reference.

GOVERNMENT INTEREST

The invention described herein may be manufactured, used, and licensed by or for the United States Government.

FIELD OF USE

The invention relates to detection of force. More specifically, the invention related to detection of blast or blunt forces such as those impacting a person or vehicle.

BACKGROUND

The field of clinical neurology remains frustrated by the recognition that secondary injury to central nervous system tissue associated with physiologic response to an initial insult resulting from direct blunt force or the percussive forces found in close proximity to a blast source could be lessened if only the initial insult could be rapidly diagnosed or characterized. While the diagnosis of severe forms of such insults damage is straightforward through clinical response testing and computed tomography (CT) and magnetic resonance imaging (MRI) testing, these diagnostics have their limitations in that medical imaging is both costly and time-consuming while clinical response testing of incapacitated individuals is of limited value and often precludes a nuanced diagnosis. In many instances, the instrumentation necessary for these diagnostic procedures is not available in many situations such as in the field. Additionally, owing to the limitations of existing diagnostic tests and procedures, situations exist under which a subject experiences a stress to their neurological condition such that the subject often is unaware that damage has occurred or does not seek treatment as the subtle symptoms often quickly resolve. The lack of treatment of mild to moderate challenges to neurologic condition of a subject can have a cumulative effect or subsequently result in a severe brain damage event having a poor clinical prognosis.

An analysis of the mechanisms and development of biomarkers related to blast injury is complicated by a deficiency in the number of quality experimental studies, and by the lack of sensitivity and specificity of biomarker based injury prediction. By the time a biomarker analysis is performed, the subject may be already in a severe and irreversible state. Thus, there is a need for a detection system that can identify the presence or absence of an event severe enough to warrant monitoring or treatment and optionally quantify the extent of trauma an individual has received that will allow for rapid treatment decision making in the field or in a clinical setting.

SUMMARY

The following summary is provided to facilitate an understanding of some of the innovative features unique to embodiments of the present invention and is not intended to be a full description. A fall appreciation of the various aspects of the invention can be gained by viewing the entire specification, claims, drawings, and abstract as a whole.

A molecular biosensor is provided that allows tor laboratory or field detection of an event, for example an event created by a blunt force or a blast force. Such events are commonly found to be the cause of traumatic, injuries such as traumatic brain injuries. As used herein, an "event force" is any force type suitable to produce or model a traumatic brain injury of any form. Such forces include, but are not limited to, blunt force, ballistic force, shock wave forces illustratively those associated with blast trauma. With traumatic brain injuries and particularly with mild traumatic brain injuries there may be no external signs of injury which potentially could delay treatment or give an indication that no treatment is necessary leading to severe, often cumulative consequences. A molecular biosensor and methods provided serve as biorelevant sensors of traumatic events.

A molecular biosensor includes a lipid vesicle on or within a housing that will not appreciably alter the event force transmitted to a vesicle. A lipid vesicle is optionally tailored to include one or more lipids and optionally other molecules including proteins and cholesterol, among others to serve as a model similar to the plasma membrane of brain tissue.

Illustrative biochemical components of a lipid vesicle in a biosensor comprise phosphatidylcholine, phosphatidylserine, phosphatidylethanolamine, phosphatidylinositol, sphingomyelin, cholesterol, ceramide, and one or more proteins—for example, integral membrane proteins, NMDA cell surface receptors, rhodopsin, ion channel transporters, and proteins that function to regulate ion transport across the membrane. Biophysical experiments to elucidate the fundamental biochemistry of mild traumatic brain injury or Alzheimer's disease will employ such membrane-protein combinations to study the effects of perturbations of the structural integrity of the sensor constructs. While such model membrane systems have not been constructed for these purposes, a variety of biochemical protocols can be applied in the synthesis of both phospholipid-based liposome assembly, as well as synthetic lipid constructs from which liposome can be assembled, or combinations thereof. The vesicles range in diameter from about 20 to about 80 nanometers according to size exclusion chromatography.

In embodiments the molecular biosensors are useful for the detection, diagnosis, or study of a traumatic event such as a blunt force, blast force, or other force of sufficient, magnitude to produce a traumatic brain injury in an animal subject, optionally a human subject. In embodiments, by affixing a molecular biosensor to a subject, an article of protective clothing or another location on a subject, the magnitude of an event can be readily ascertained, which could be used to direct the wearer to medical attention if necessary or for the study of the ability of protective articles to protect a subject.

The biosensors and methods provided address the need for a biologically relevant correlation to traumatic injuries that can be used in either a field or laboratory setting.

DETAILED DESCRIPTION

The following description is exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes are described as individual steps or using specific materials, it is appreciated that described steps or materials may be interchangeable such that the description of the invention includes multiple parts or steps arranged in many ways as is readily appreciated by one of skill in the art.

A significant technology gap exists in the testing of personal protective equipment for subject individuals and animals, relating to body armor as well as helmet systems, and other protective equipment. Sensors are required to determine the correlation between threats (insults) to the subject so as to provide a means by which protective equipment can be assessed for its ability to protect a subject from a variety of insults and injury, and to optimize the design trade-offs between armor weight, thickness, energy dissipation, stopping power, and the like. This need extends to the widely publicized concerns regarding protection of subject in conflict or competitive areas, and to the protective measures needed for contact sports, for example, American football.

Recent understanding of the medical conditions known as traumatic brain injury (TBI), chronic traumatic encephalopathy (CTE), certain aspects of post traumatic stress disorders (PTSD), and their associated symptoms, further illuminate the need for improved understanding of the effects of severe trauma to the head, limbs or torso. Improved prophylaxis includes armor designed to better shield from the insult scenarios—as well as improved post exposure treatment to alleviate or minimize the short and longer term effects of the insults. A gamut of intracranial pathologies results in symptoms including loss of memory, disorientation, angiogenesis, and long-term cognitive disorders.

Clearly a means is required by which the range of insults, including blunt trauma, ballistic impact (often collectively referred, to as B&B), and shock trauma, can be measured with a metric that directly indicates the injury to the body due to an insult thereby directly correlating insult to injury. While a host of sensors have been employed to this end—including pressure sensors, accelerometers, strain sensors, and optical surface measurement methodologies, to characterize the energy impacting the protective armor, and the dissipation of that energy through the human tissues—and a range of torso and head form anthropomorphic test modules (ATM) incorporating these sensors, the point and 2-dimensional energy characterizations, along with time resolved networked sensor determinations—have all provided a less than satisfactory correlation of insult to injury. While a host of candidate sensors continue to emerge in the literature (hydro gels, functionalized nanoparticles, photonic crystals, etc.), only the novel sensor concept disclosed herein directly represents the response of human tissues to traumatic insult. Nanotechnology research is replete with examples of self assembled chemicals forming well controlled supramolecular films and structures, including manipulation of material properties at the atomic level of detail.

Problems with current sensors used in test labs include the lack of repeatable measurement, poor to no correlation, lack of calibrated response to the range of insults to include ballistic threats; and concurrently, lack of correlation to any or all of the range of tissue susceptibilities and widely varying vulnerabilities. Test artifacts abound due to a wide range of variables, including threat mass, velocity, total yaw at impact, yaw cycle precession, obliquity at impact, backing material variability, along with backing material inconsistencies, tissue simulant variation, and lack of controlled test protocols proving repeatability of test metrics. This results in highly conservative limits for penetration depth at prescribed impact kinetic energies, providing only partially correlated determination of armor suitability—and little trade space for the armor designer to effect improvements.

Bullets and fragments cause tissue injury a number of ways, even if the impact is nonpenetrating. The amount of kinetic energy transferred to the tissues correlates to the severity of the tissue damage, which is determined by four key factors. Cooper, G J., and J. M. Ryan. Br J Surg., 1990; 77:606-610. These include kinetic energy ($\frac{1}{2}mv^2$) at impact, total yaw at impact, shape of the insult, and the characteristics of the target tissue (density, strength, and elasticity). The complete disclosures of the above references are incorporated herein by reference. Nonpenetrating events causing tissue damage mechanisms may be collectively addressed as the disruption of the phospholipid bilayer surrounding the cellular structure of human tissues. Relative damage to tissues correlates directly to tissue densities; such that a measure of lipid bilayer disruption by the threat provides a very direct and novel approach to the lingering problem of insult to injury correlation.

The drawbacks of prior sensor systems and processes of their use are addressed by a physiologically relevant sensor such as those provided. A sensor is provided as well as processes for using a sensor for detection of a traumatic event and, more specifically, a biosensor for detecting percussive, blunt force, or other trauma. Such sensors can be used to test the ability of protective equipment to protect an individual's brain or other organs from certain traumatic events. Thus, a device is provided that can be used to provide an indication of whether a traumatic event may have caused a traumatic brain injury and to a sensor that can be used to determine the ability of protective equipment to protect against particular threats. The invention has utility as a detector and method of detecting the presence or absence of an event sufficient to produce a traumatic brain injury such as mild traumatic brain injury (mTBI) or other traumatic brain injury.

In embodiments the present invention involves the use of self assembled liposomes. As used herein, self assembly of liposomes refers to the thermodynamically stable assembly, in solution, of lipids into the characteristic spherical structures known as liposomes. Hydrophilic acyl tails extend towards one another inside the phospholipid bilayer, and hydrophilic head groups orient toward the aqueous environment, both inside and outside the bilayer.

In embodiments, liposome structures are utilized as a sensor for an event, illustratively an event sufficient to cause mild traumatic brain injury or traumatic brain injury. The sensor is configured and packaged in a manner where the sensors can be affixed to a subject's helmet, body armor or other personal protective equipment and provide a direct indication of the trauma received at the point of attachment. Packaging configurations will depend on the applications. For perfusion of mimetic brain tissue or gels, the sensor will remain in solution and be perfused into and through brain tissue and surrogates. For the example of use on a Soldier's helmet or body armor attachment, the liposomes will likely be affixed to gels and the sensing mechanism will occur as the colorimetric changes occur in and on the gels. As an alternative to the gel encapsulation, the liposome solutions will be contained in a pill capsule. In still further embodiments, they can also be contained in quartz cuvettes used to insert the solution directly in the circular dichroism meter. This trauma indicator relates to and is equivalent to the blunt and ballistic trauma, as well as the convolved effect of shock waves associated with blast trauma, received by the human body tissues during equivalent events. The sensor, therefore, represents the first real and direct measure by which insult is correlated to injury. The disruption of the phospholipid bilayer occurring to a human or other subject representing damage to a subject's tissue is the very same disruption measured by a sensor in embodiments of the instant disclosure. Thus, in certain embodiments a sensor of the present invention is believed to provide a more accurate measure of damage to tissue caused by a blast.

A further beneficial embodiment is to embed the vesicles in a gel and use either confocal or two-photon microscopy (both available in our laboratories) to image the leakage of embedded dyes. Additionally, changes in trans-membrane protein function due to trauma can be implemented in Hodgkin-Huxley-like model neurons by altering parameters representing the fraction, conductance, and reversal potentials of simulated voltage gated channels. Changes in lipid bi-layer permeability can be modeled through changes in leakage current conductance.

In embodiments, a molecular biosensor is provided that includes a lipid vesicle (liposome) and a housing. The lipid vesicle is associated with the housing such as being contained within the housing or otherwise attached to or retained by the housing. An event such as a shock wave or blunt force when contacting the housing is transmitted to the lipid vesicle causing alteration in a molecular characteristic of the vesicle that correlates with and indicates the degree, type, duration, severity, or other characteristic of the event force.

A lipid vesicle is sufficiently related to the plasma membrane of a brain cell. Sufficiently related means that the lipid vesicle is possessing similar lipid and, optionally, protein content to the plasma membrane of a brain cell such that molecular alterations in the vesicle correlate to damage of a neuron when exposed to an event force. Vesicles that are sufficiently related possess a lipid composition having phosphatidylcholine (PC) and/or phosphatidylethanolamine (PE) as the major lipid component. As such, embodiments of a molecular biosensor include lipid vesicles comprising phosphatidylcholine, phosphatidylethanolamine, or have a lipid content that is 50% or greater a combination of phosphatidylcholine and phosphatidylethanolamine. Illustrative examples of the lipid content of the plasma membrane are illustratively found in Scandroglio, et al., *J Neurochem*, 2008; 107 (2): 329-338. The complete disclosure of which is incorporated herein by reference. In some embodiments, the amount of lipid (e.g. phospholipid, sphingomyelin, and cholesterol) is represented by the amounts presented by Scandroglio et al., for example from about 20 percent to about 70 percent molar ratios.

A lipid vesicle is optionally formed from phosphatidylcholine, phosphatidylethanolamine, phosphatidylserine (PS), phosphatidylinositol (PI), sphingomyelin, cholesterol, ceramide, or combination thereof. In embodiments, a lipid vesicle comprises from about 50 to about 100 percent phosphatidylcholine or a combination of phosphatidylcholine and phosphatidylethanolamine. Lipid vesicles optionally contain only phosphatidylcholine as a lipid component. In other embodiments, the concentration of phosphatidylcholine is from about 30 to about 80 percent of total lipid weight. For example, we are currently examining the PC:cholesterol molar ratios of 7:3 and 1:1, at both 200- and 400-nm liposome diameters, saturated with calcein self-quenching dyes, at 10 mg/ml total lipid concentrations.

A lipid vesicle may further comprise phosphatidylserine in an amount of from about 5 to about 30 percent of the total lipid weight.

In a separate embodiment, a lipid vesicle comprises sphingomyelin in an amount of from about 1 to about 30 percent of the total lipid weight. In other embodiments, the lipid vesicle comprises sphingomyelin in an amount of from about 5 to about 30 percent of the total lipid weight.

Some embodiments include phosphatidylcholine/PE/PS combinations where the phosphatidylcholine/phosphatidylethanolamine is present in an amount of from about 5 to about 30 percent of the total lipid weight.

Lipid vesicles may further comprise cholesterol. Cholesterol is optionally present at an amount relative to the lipid portions of 0.5 cholesterol/lipid or less by molar ratio. In some embodiments, the amount of cholesterol is present at a ratio of 0.01 to 0.5 cholesterol/lipid or any value or range there between.

It is appreciated that lipid vesicles may contain other materials comprising proteins or fragments of proteins that may or may not alter the fluidity of the membrane or provide a membrane with a protein content similar to that of a brain neuron as is known in the art. These include for example integral membrane proteins such as cell surface receptors and trans-membrane proteins. It is further appreciated that while the lipid vesicles described are provided as examples, lipid vesicles may comprise phosphatidylcholine, phosphatidylethanolamine, PS, PI, cholesterol, ceramide, sphingomyelin, and protein in any combination and all combinations are appreciated as envisioned under the invention. In some embodiments, a lipid vesicle includes PC alone to the exclusion of other lipids, cholesterol, or protein.

Methods of forming a lipid vesicle are well known in the art. The experimental platforms will ultimately allow us to determine relationships between mechanical forces and disruption of lipid bilayers and integral membrane proteins. In embodiments, the novel sensor will allow us to reduce the complexity of the interaction between insult mechanisms and trauma to the response of individual membrane properties, individual trans-membrane proteins, and extracellular scaffolding properties. This can occur without needing to account for cotemporaneous changes across multiple interacting mechanisms as is the case with whole-cell models. The sensor will also be used to explore and understand the biochemical pathways associated with mTBI. The sensor allows us to isolate and study known integral membrane proteins, associate disruption of these proteins and the resultant downstream translation of biomarker proteins, and start to assemble the set of reaction kinetics and network models for each parallel effect. This will then allow for the solution of simultaneous reaction equations to further elucidate the nature of mTBI at the biochemical level.

Methods of forming a lipid vesicle are applicable to the formation of lipid vesicles provided herein as a portion of a biosensor. For example, lipid vesicles formed by techniques for assembly of the liposome structures are well characterized, since liposomes are the basis for several novel drug delivery systems and therefore well developed. The basic process involves hydration of dry lipid, cholesterol, protein or other component of the lipid membrane onto a vessel surface from organic solvent (e.g. chloroform) thereby producing a thin film of dry lipid. This material is then hydrated to solution typically in an aqueous buffer system such as Tris buffered saline, HEPES buffered saline, water, or other suitable buffer known in the art, and forming the liposomes as the solution is heated above the liposome phase transition. As many lipids have a phase transition that is below room temperature, heating is not always necessary depending on the total composition of the lipid membrane. Concentric lipid bilayers result, in the form of controlled 30-70 nm diameter liposome spheres. Freeze-thaw processing further refines the liposome morphology. As such, in some embodiments, lipid vesicles are formed by sonication of the hydrated material typically on ice to prevent overheating, or by one or more freeze-thaw cycles. The resulting liposomes are optionally sized by chromatography or by passing through one or more filters of desired pore size.

In some embodiments, a lipid vesicle comprises one or more detection agents. A detection agent is optionally any molecule that is encapsulated by a lipid vesicle that can be released upon vesicle rupture and thereby detected. Illustrative examples of detection, agents include dyes, fluorophores, nucleic acids, proteins, combinations thereof, and the like. By encapsulating one or more detection agents in the liposome (either in the space within the liposome or the lipid monolayer, bilayer, or multilayer) during the self assembly process, a lipid vesicle is provided that will allow a detectable color or other change from the trauma induced liposome disruption that is proportional to the amount of disruption or insult. This affords a very attractive additional feature, whereby a color change readily observed by direct visual observation provides indication that more precise measurement should be taken of the subject as the basis for determination of prophylaxes and post trauma expectations. Epidemiological data can also be accumulated rapidly for further assessment of various treatment options to save lives and minimize post insult conditions.

Illustrative examples of a detection agent include fluorophores such as calcein, pyranine (1-hydroxypyrene-3,6,8-trisulfonic acid), and FAM dye (illustratively 6-carboxyfluorescein). Other fluorophores illustratively include TAMRA, AlexaFluor dyes such as AlexaFluor 495 or 590, Cascade Blue, Marina Blue, Pacific Blue, Oregon Green, Rhodamine, Fluorescein, TET, HEX, Cy5, Cy3, Quasar670, and Tetramethylrhodamine. Specific examples of fluorophores include 5- (and -6)-carboxyfluorescein mixed isomers (CF), Alexa Fluor 647 carboxylic acid, succinimidyl ester (Alexa 647) each available from Life Technologies, Grand Island, N.Y.

Other illustrative examples of a detection agent include the pH sensitive dyes. An illustrative example of a pH sensitive dye is acridine orange and the like.

A detection agent may further comprise a nucleic acid sensitive agent. An illustrative example of a nucleic acid sensitive agent is illustratively Hoechst 33342 (2,5'-Bi-1H-benzimidazole, 2'-(4-ethoxyphenyl)-5-(4-methyl-1-piperazinyl)). The casein dyes are similarly nucleic acid sensitive.

In some embodiments, a detection agent is bound to a retention molecule to prevent leakage from the lipid vesicle prior to rupture. Such retention agents are any membrane inert material such as biotin, polyethylene glycol, antibodies, or other materials known in the art.

In some embodiments, a detection agent is nucleic acid sensitive. A nucleic acid is optionally bound to a surface of a housing such as by reaction with a polystyrene plate. A nucleic acid molecule is optionally animated to promote binding to a polystyrene section of a housing via the amine bond. Illustrative technology is available from Corning, Inc. Tewksbury, Mass. sold as the DNA-BIND® polystyrene material. A nucleic sensitive dye such as 4',6-diamidino-2-phenylindole (DAPI), or the cell impermeant SYTOX® Green nucleic acid stain. When a nucleic acid sensitive dye is released upon lipid vesicle rupture, it will bind a nucleic acid molecule on the surface of the housing localizing colorimetric detection of lipid vesicle rupture.

In further embodiments, a detection agent comprises a nucleic acid, antibody, protein, or other molecule suitable for specific interaction with a binding partner. Illustratively, a nucleic acid is used such as a nucleic acid that is suitable as a primer for a polymerase chain reaction. Extraction of a portion of the extraliposomal solution and its inclusion in a PCR reaction will positively or negatively discern whether the nucleic acid based molecule has leaked from the lipid vesicle.

Other detection agents include antibodies that can specifically bind to an antigen bound to a surface of a housing. The housing surface can then be probed by a process similar to an enzyme linked immunosorbent assay (ELISA) to detect the presence or absence of the antibody. It is appreciated that other detection agents are similarly suitable.

Freeze-thaw processing during lipid vesicle formation (e.g. 2-3 cycles) further refines the liposome morphology and provides for encapsulation of one or more detection agents from a biphasic mixture for colorimetric sensor features. Note that certain fluorophores are activated upon exposure to solvent reagents and or water, thereby effecting the color change for direct insult observation. As such in some embodiments, one or more fluorophores are encapsulated in a lipid vesicle formed in a non-aqueous solution. The resulting vesicles are then washed and placed in an aqueous medium for association with a housing. Upon rupture due to an event force, the detection agent escapes the lipid vesicle and is detectable by a direct color change. This provides rapid and easy identification of a situation requiring medical attention to the wearer of the biosensor.

The liposome based sensor can be incorporated in the variety of anthropomorphic test modules and instrumented head forms (collectively housing) currently available, supplanting or at least supplementing the less effective pressure sensors and accelerometers that previously provided far less than optimal correlation to mild traumatic brain injury or traumatic brain injury at best. As the applications are validated for the sensor, a variety of housing options are available. These include lamellar encapsulation of the liposomes themselves, incorporation in solution, and containment in honeycomb interlaced sheets of material as well as tablets or ampoules for convenient attachment at vulnerability points of interest. Arrays of the sensors can also be implemented to provide dimensionality and spatial control of the event characterization. Placement of the sensor as close as possible to the vulnerable areas of concern thus provides a direct and more accurate measure of the tissue susceptibility to a threat combination or singular test scenario.

A housing is either a surface whereby the lipid vesicles are exposed directly to the environment, or the housing encapsulates the lipid vesicles whereby the housing has at least one surface that will transmit an event force from the external environment to the lipid vesicle. In an embodiment, at least one portion of a housing is transparent to a wavelength of light emitted or reflected by a detection agent. In another embodiment, a housing is in a capsule form. In a further embodiment, a housing is in a cubic or rectangular prism form. In yet another embodiment, a housing is in a spherical, sheet, curvilinear, or other two-dimensional or three-dimensional shape. One example of a suitable housing is similar to a dialysis cassette. In embodiments such a housing has a membrane on one or both sides that will transmit an event force to a lipid vesicle contained within the housing. Such embodiments also provide the ability to encapsulate one or more detection agents into the vesicle and then transfer buffer or wash away any excess dye after vesicle formation simply by buffer exchange right in the housing.

Optionally, a housing is in the form of a capsule. Capsules can be formed of any material traditionally known in the art that will transmit an event force to a lipid vesicle. Illustrative materials comprise gelatin, starch, casein, chitosan, soya bean protein, safflower protein, alginates, gellan gum, carrageenan, xanthan gum, phtalated gelatin, succinated gelatin, cellulosephtalate-acetate, oleoresin, polyvinylacetate, hydroxypropyl methyl cellulose, polymerisates of acrylic or methacrylic esters, polyvinylacetate-phtalate and combinations thereof.

A housing is optionally formed in whole or in part of polymeric materials. Illustrative examples include flexible vinyls (e.g. polyvinylchloride), polyamides, polypropylene, norell, polysulfone, ABS, polyethylene, natural and synthetic rubbers, among many others.

The molecular biosensors provided have the capability to detect, measure, quantify, and optionally correlate an event force to the likelihood or severity of traumatic brain injury or mild traumatic brain injury suffered by a wearer of the biosensor. As such, processes of detecting and, in some embodiments, quantifying blast or other direct event force using self assembled liposome structures as a unique sensor are provided. The liposome structures are configured and packaged in a manner where the sensors can be affixed to a subject's clothing, a helmet, body armor, or personal protective equipment in a manner that provides direct indication of the trauma received at the point of attachment. As such, in some embodiments, a molecular biosensor is affixed to an item of clothing or protective equipment such as a helmet or to a traditional clothing form. A molecular biosensor is optionally affixed to a building or vehicle surface. A molecular biosensor has utility for the detection of blunt and ballistic trauma, as well as the convolved effect of shock waves associated with blast trauma, received by the body tissues of a subject during equivalent events. The sensors provided represent the first real and direct measure by which insult is correlated to injury. The disruption of the phospholipid bilayer in human tissue resulting from such forces is directly measured by the liposome sensors in the in the most meaningful way possible—by the identical disruption that occurs to a subject.

An apparatus and process of detecting a traumatic event is provided including subjecting a molecular biosensor to an event force, and analyzing the biosensor or lipid vesicle portion for alteration indicative of an event force sufficient to produce traumatic brain injury or mild traumatic brain injury in a subject subsequent to the initial trauma. A shock wave generator is one possible source of an event force. A blunt force trauma is optionally produced by any source of such force. Experimentally blunt force events are produced by fluid percussion, cortical impact and weight drop/impact acceleration sources.

A molecular biosensor is used in a process of detecting a traumatic event, or a lipid vesicle absent a housing is used. The presence or absence of a traumatic event is determined by an alteration in the lipid vesicle itself or by an alteration in the amount, type, binding, or other characteristic of a detection agent present in the lipid vesicle or on the lipid vesicle.

In embodiments, a traumatic event is determined by an alteration in the molecular structure or orientation of one or more molecules that make up a lipid vesicle. Illustratively, circular dichroism is used to detect molecular alterations in one or more components of a lipid vesicle. The sample material to be analyzed is contained in a quartz cylinder, within which are spacers to accommodate smaller sample vessels. An alternate sample container comprises a Hellma Analytics photometric micro tray cell cap. Alternate packaging schemes may be developed to provide insult maps across curved and rectilinear tessellations for certain applications. Linearly polarized light is passed through the analyte. In a chiral material such as the liposome, the right and left circularly polarized components travel at different velocities and are differentially absorbed. This results in the light exiting the analyte with elliptical polarization, and the analyte is deemed to possess circular dichroism (CD). The magnitude of CD is expressed as the molecular ellipticity θ:

$$\Theta = 4500/\pi(\epsilon_L - \epsilon_R)\log_e 10 \tag{1}$$

where $\epsilon_L$ and $\epsilon_R$ represent the molecular extinction coefficients for the right and left circularly polarized light beam components. The difference between the extinction coefficients is:

$$\Delta\epsilon = (\epsilon_L - \epsilon_R) = 1/LC \log_{10}(I_R/I_L) \tag{2}$$

where L is the absorbing layer thickness (cm), C is the molar concentration, $I_R$ and $I_L$ are the intensities of the right and left circularly polarized light beams after passing through the analyte. θ then becomes:

$$\Theta = 4500/\pi LC \ln 10 \log_{10}(I_R/I_L) \tag{3}$$

Circular dichroism spectrometers such as the J-815 from Jasco Corporation, Easton, Md., measure CD changes of the magnitude produced in the sensor. Differential CD is created by disruption of the intramolecular chiral interactions of three-dimensional molecular structures—as well as the additional chiral symmetry breaking of nonchiral molecules in the sensor material construction. Measurement in changes of CD are indicative of alterations in the structure of the lipid vesicle and indicative of an event force.

In embodiments, a traumatic event is detected by analysis of a medium external to a lipid vesicle. For example, and in embodiments, a lipid vesicle includes one or more detection agents within the vesicle. The leakage of a detection agent(s) into the extraliposomal space is indicative of damage to the lipid membrane such as rupture or more minor damage. Optionally, a detection agent is a fluorophore. In embodiments, the fluorescence is quenched due to high dye concentration internal to the liposome, and unquenched upon release of the dye molecules into the surrounding solvent upon event force. Instrumented techniques based on atomic force microscopy, confocal fluorescence microscopy, and fluorescence recovery after photo bleaching (FRAP) optionally coupled with colorimetric fluorometry (detection of light intensity based on leakage of dye from the disrupted cell wall) are used to analyze liposome disruption and failure criteria. The rate of detection agent release is optionally accomplished through cholesterol-influenced bilayer properties where higher levels of cholesterol typically equate to a less fluid and more event force resistant membrane.

The molecular biosensors and processes provided find usefulness in many arenas such as in military applications for the design of protective equipment such as: body armor and helmets; rapid diagnosis or prediction of possible traumatic brain injury or mild traumatic brain injury in a subject receiving an event force in the field to provide or indicate the need for medical intervention; as a point sensor or array of sensors to provide 2-D mapping of trauma; as a sensor useful in the design and use of sport related protective headgear in which concussions and other brain injuries are a concern; as a sensor for research, testing and/or development of protective equipment by athletic equipment manufacturers and military equipment manufacturers; and as a research tool for the understanding of the molecular results of forces that produce traumatic events and complications such as traumatic brain injury or mild traumatic brain injury.

Various modifications of the present invention, in addition to those shown and described herein, will be apparent to these skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof.

The invention claimed is:

1. A molecular biosensor for determining blast, ballistic and blunt trauma comprising:
   a lipid vesicle comprising a detection agent;
   a housing, said vesicle contained on or within said housing, said housing having a portion capable of transmitting a blast, ballistic or blunt traumatic force generated external to said housing to said vesicle;
   wherein said vesicle comprises phosphatidylcholine, phosphatidylserine, phosphatidylethanolamine, phosphatidylinositol, sphingomyelin cholesterol, ceramide, or combinations thereof;
   wherein the phosphatidylcholine, phosphatidylserine, phosphatidylethanolamine, phosphatidylinositol, sphingomyelin cholesterol, ceramide, or combinations thereof are inserted into a circular dichroism (CD) meter to measure a differential absorbance of left and right circularly polarized light; and
   further wherein a differential circular dichroism is created by disruption of intramolecular chiral iterations of three-dimensional molecular structures as well as a chiral symmetry breaking of nonchiral molecules in a sensor material construction.

2. The biosensor of claim 1 wherein said vesicle consists of phosphatidylcholine.

3. The biosensor of claim 1 wherein said vesicle comprises greater than 50 percent total lipid of phosphatidylcholine, phosphatidylethanolamine, or a combination thereof, and
   wherein said housing is in the form of a lamellar structure, interlaced sheet, capsule, or tablet.

4. The biosensor of claim 1 wherein said housing is in the form of a capsule.

5. The biosensor of claim 1 wherein said vesicle further comprises a detection agent.

6. The biosensor of claim 1 wherein said detection agent consists of a fluorophore.

* * * * *